United States Patent [19]

Herb

[11] 3,951,148

[45] Apr. 20, 1976

[54] BLOOD COMPONENT STORAGE BAG AND GLYCEROLIZING SET THEREFOR

[75] Inventor: John R. Herb, Easton, Pa.

[73] Assignee: Pharmachem Corporation, Bethlehem, Pa.

[22] Filed: May 29, 1974

[21] Appl. No.: 474,182

[52] U.S. Cl. .............................. 128/272; 128/214 D; 150/8; 222/107

[51] Int. Cl.[2] .............................................. A61M 5/14

[58] Field of Search ........ 128/214 R, 214 C, 214 D, 128/214.2, 227, 272, 275; 222/107, 215, 462; 150/8

[56] References Cited

UNITED STATES PATENTS

| | | | |
|---|---|---|---|
| 2,210,098 | 8/1940 | Ravenscroft | 128/214 R |
| 2,261,065 | 10/1941 | Kirchner | 128/214 R |
| 2,323,629 | 7/1943 | Spanel | 150/8 X |
| 3,030,955 | 4/1962 | Gossett et al. | 128/272 |
| 3,105,613 | 10/1963 | Barton et al. | 128/272 X |
| 3,205,889 | 9/1965 | Alder et al. | 128/214 D X |
| 3,316,908 | 5/1967 | Burke | 128/214 C |
| 3,328,255 | 6/1967 | Ilg | 128/214 D |
| 3,506,130 | 4/1970 | Shaye | 128/214 C X |
| 3,509,879 | 5/1970 | Bathish et al. | 128/272 X |
| 3,554,256 | 1/1971 | Anderson | 128/214 D X |
| 3,746,001 | 7/1973 | Ralston | 128/214 D |

FOREIGN PATENTS OR APPLICATIONS

| | | | |
|---|---|---|---|
| 1,404,624 | 5/1965 | France | 128/272 |

*Primary Examiner*—Dalton L. Truluck

[57] ABSTRACT

Bag for storing blood components, preferably frozen red blood cells, including specifically an inlet-outlet fitment, the inlet consisting of a hollow outward protrusion with a circumferential raised portion on its outer diameter adapted to sealingly receive a flexible tube whereby the bag may be interconnected with a variety of other blood storage or treatment devices. In the preferred form of this invention, the bag is combined with a glycerolizing set consisting of a first flexible resilient tube adapted to sealingly mate with the inlet protrusion of the bag and communicate with a Y connector, which connector further communicates through second and third resilient tubes with a drip chamber connected to a hollow spike for puncturing a container such as a glycerin container and with a second hollow spike for puncturing a container, such as a container of red blood cells, and for drawing fluid therefrom. The tubes connected to the Y connector may include a means external thereof for restricting fluid flow therein to facilitate use of the apparatus.

1 Claim, 4 Drawing Figures

BLOOD COMPONENT STORAGE BAG AND GLYCEROLIZING SET THEREFOR

This invention pertains to a bag for storing blood components which is readily adaptable to a variety of uses. More particularly, this invention pertains to such a bag in combination with a simple and convenient glycerolizing set.

Sterilizable, flexible closed plastic bags of a variety of shapes and forms have been used as storage containers for blood and various blood components. In most cases, these bags have been adapted to particular uses by virtue of specific inlet and outlet configurations in combination with puncturable diaphragms and integral tubing adapted to the particular use for which the bag was intended. Undue expense and inconvenience is caused by these prior art bags due to their inherent limitation to the use for which they are intended and their relative non-adaptability to other uses.

Having in mind these problems, it is the general object of the present invention to provide a simple plastic bag adaptable to a number of blood storage uses by virtue of one or more unique inlet fitments.

With reference particularly to the inconvenience and expense of such prior art blood bags intended for freeze storage of red blood cells and the inconvenience of prior art glycerolizing sets used with such bags, it is a further object of this invention to provide a readily adaptable plastic bag for freeze storage of red blood cells in combination with a simple glycerolizing set which facilitates the glycerin treatment of red blood cells and the introduction of the glycerolized red blood cells into the freeze storage bag.

These and other objects are met, in accordance with the present invention, by a storage bag consisting of a sterilizable, flexible closed plastic container with means for hanging the container either in an upright or inverted position, the container further including an inlet-outlet fitment at the top thereof. The fitment includes an outlet comprising a first hollow outward protrusion with a removable cap and at least one inlet consisting of a second hollow outward protrusion, the second protrusion having on its outer diameter a circumferential raised portion adapted to sealingly engage the inner diameter of flexible tubing whereby the bag is connected with a variety of other blood storage or treatment devices. In the preferred form of the present invention, this bag is combined with a simple and convenient glycerolizing set the first flexible tube of which sealingly engages the inlet protrusion of the bag and communicates with a Y connector, which in turn communicates through a second resilient flexible tube with a drip chamber attached to a hollow spike for puncturing a container such as a container of glycerin to withdraw fluid therefrom. The Y connector also communicates through a third flexible resilient tube with a second hollow spike, so that the spike may be inserted in a container, such as a container of red blood cells to permit free fluid passage through the spike into and from the fluid container.

The drip chamber may consist, for example, of a transparent collapsible cylinder, of substantially larger diameter than the flexible tube to which it is connected, permitting observation of the flow rate of drips or fluid stream through the chamber. The collapsibility of the chamber provides the possibility of using the chamber as a pump by squeezing it and releasing it to cause fluid to be drawn into or forced from the chamber.

In the mating of the glycerolizing set or any other blood treatment or storage system with the bag of this invention by a flexible resilient tube mating with the one or more inlet protrusions on the fitment of the bag, a clamp may be provided to insure the sealing engagement of the tube with the inlet fitment protrusion.

In most cases, at least two of the flexible resilient tubes referred to will include an external means thereof for restricting fluid flow therein. For example, a sliding valve with a narrow channel therein fits over the tubing with an opening in the valve communicating with the channel usually surrounding the tube during unrestricted fluid passage through the tube. When it is desired to restrict the fluid passage, the valve member is slid over the tube with the narrow constriction forced to collapse the tube so as to restrict fluid flow therethrough. Preferably, a roller squeeze valve means, as shown in the illustrated embodiment of this invention, is used.

For a better understanding of this invention, reference is made to the appended claims and to the following detailed description thereof, taken in conjunction with the drawings in which:

Figure 1:
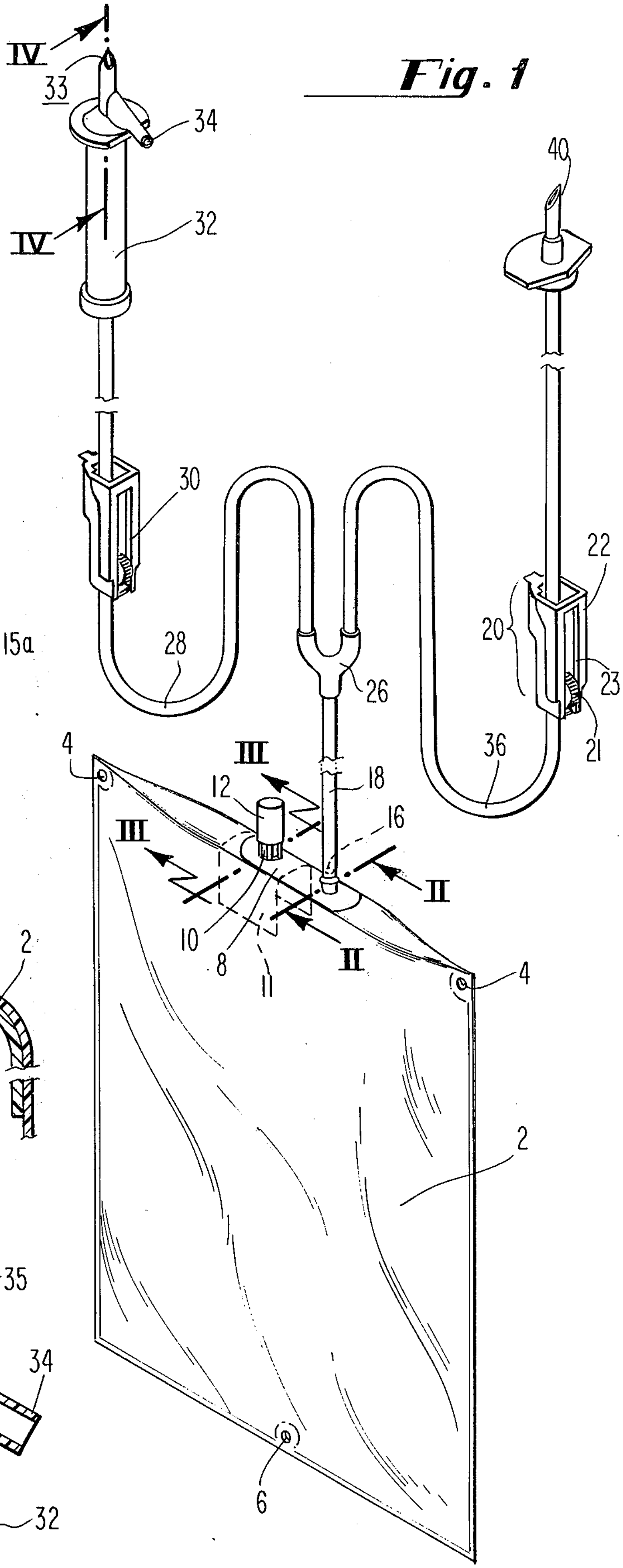
FIG. 1 is a perspective view of the blood storage bag and associated glycerolizing set of this invention.
Figure 3:
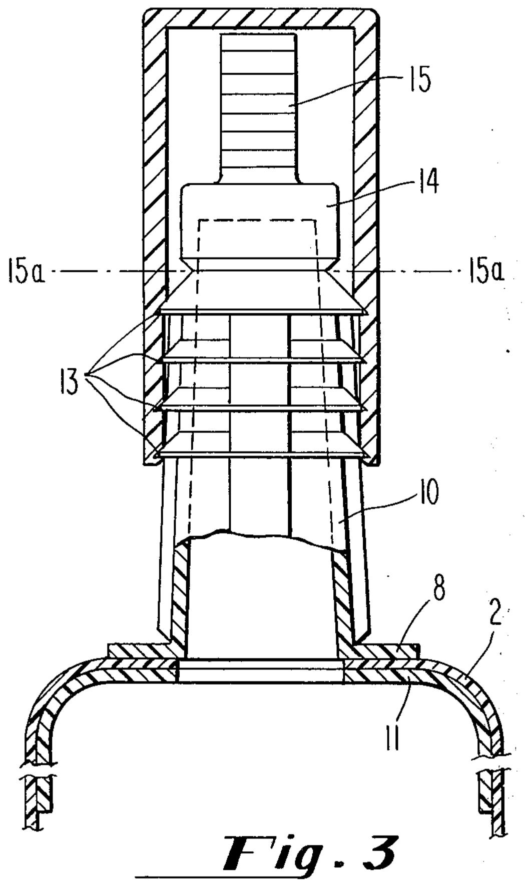
FIG. 3 is an enlarged view, partially in section, of the outlet opening and associated sealing means of the bag, on the line III—III of FIG. 1.
Figure 4:
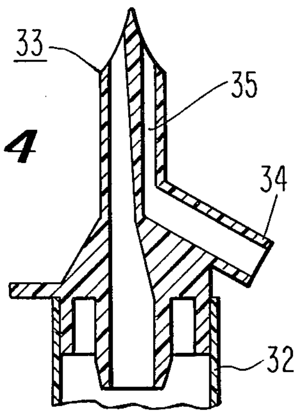
FIG. 4 is a sectional enlarged view of one component of the apparatus, on line IV—IV of FIG. 1.

Turning now to FIG. 1, there is shown a sterilizable, flexible plastic bag 2 with means consisting of hanging holes 4 and 6 for hanging the bag either in an upright or inverted position. Bag 2 also includes a closure fitment 8 including first hollow outward protrusion or neck 10 comprising the outlet opening in the bag. As better seen in the enlarged and partially sectional detail view of FIG. 3, neck 10 is located over a member 11 in bag 2. A removable outlet cap 12 encloses neck 10, with engagement between cap 12 and sealing ridges 13 providing a protective seal. As shown in FIG. 3, there are four sealing ridges 13 on the neck 10 and the cap 12 has a reduced internal diameter above the point of engagement of the cap with the topmost sealing ridge 13, thus providing a stop for preventing the cap from further downward movement on the neck 10. In the preferred form of this invention, ridges 13 are designed for about a 0.005 inch interference fit with cap 12 or, as illustrated, mating annular internal grooves for engaging the sealing ridges 13 may be provided internally of the cap 12. An integrally molded inner cap 14 includes a tear tab 15. In preparing to use neck 10, cap 14 is torn from the outer tip of neck 10, separating along a tear line 15*a* of thin plastic.

Figure 2:
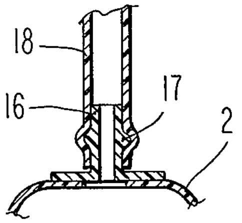
FIG. 2 is an enlarged sectional view of the closure fit on the inlet opening of the bag, on the line II—II of FIG. 1.

Closure fitment 8 (as better seen in the enlarged sectional view of FIG. 2) also includes at least one inlet comprising a second outwardly hollow protrusion or neck 16. Neck 16 also includes a ridge or circumferential raised portion 17 on its outer diameter. Closure fitment 8, particularly includng necks 10 and 16, provides a convenient and simple means for adapting bag 2 to any of a variety of blood storage applications, including the storage of various blood components such as the freeze storage of red blood cells.

As shown, in the preferred form of the present invention, neck 16 sealingly mates with a flexible resilient tube 18, the inner diameter of which corresponds to the outer diameter of neck 16 so as to facilitate this sealing engagement of these elements.

In some cases, an outer clamp such as a C clamp over resilient tube 18 may be used to insure the sealing or engagement of tube 18 with the inlet protrusion 16.

Tube 18 is connected to Y connector 26, the other two legs of which are connected first to second flexible resilient tube 28 having mounted thereon a second valve member 30 providing a controllable fluid flow restrictor as may be required in the functioning or use of the apparatus. Second tube 28 communicates with drip chamber 32, consisting of a relatively large diameter transparent collapsible symmetrical chamber attached to a hollow puncturing spike 33, in which is incorporated an integral air vent 34 and passageway 35 (as better seen in the enlarged sectional view of FIG. 1). The remaining leg of Y connector 26 is connected to a third flexible resilient tube 36. Tube 36 is connected to a second hollow puncturing spike 40 and fluid flow therein is controlled by means of a valve means 20 with a roller 21 mounted in an inclined channel of valve housing 22. A portion of roller 21 protrudes through a lengthwise opening 23 in housing 22. Tube 36 passes between roller 21 and an opposed inclined face within housing 22. With roller 21 at the wider end of housing 22, fluid may flow freely through tube 36. Movement of roller 21 toward the narrow end of housing 22 squeezes tube 36 between roller 21 and the opposing inclined face of housing 22 restricting fluid flow through tube 36. Valve means 30 is similar in design and operation to member 20. While these forms of valve members are preferred, a simple slotted restrictor may also be used to control fluid flows.

In the use of the bag and glycerolizing set of the present invention, particularly in the use of the glycerolizing set in conjunction with the use of the bag as a freeze storage container for red blood cells, fluid flow in tube 28 is first restricted by valve means 30 and drip chamber 32 is partially collapsed, such as by squeezing it. Spike 33 is then inserted in a resilient closure cap of a container of glycerin or other suitable red blood cell preservative and the pressure on drip chamber 32 is relaxed, whereby glycerin is drawn into it and at the same time air is drawn into the glycerin container through the air passageway 35 of the spike 33. Spike 40 is inserted in a container of red blood cells and, with valve means 20 and 30 in an open position and with both the glycerin container and the red blood cell container lowered below the neck 16, the glycerin container is raised or the red blood cell container is lowered so that glycerin enters the red blood cell container. After about 100 milliliters of glycerin has passed into the red blood cell container, fluid flow is constricted by enclosure of valve means 20 and 30. After permitting the partially glycerolyzed red blood cells to equilibrate for 5 to 10 minutes, the glycerin container and the red blood cell container are raised above the bag 2, valve means 20 is opened and the contents of the red blood cell storage container are permitted to flow into bag 2. Valve means 30 is then opened and the remainder of the glycerin passes into bag 2.

The glycerolizing set is then sealed from the bag 2 (by a squeeze clamp on the tube 18, for example) approximately one-half inch above the inlet protrusion or neck 16 and the glycerolizing set is then separated from the red cell freezing bag by cutting the tube 18 above the seal whereupon the treated red blood cells in bag 2 are ready for freeze storage.

While this invention has been described with respect to specific embodiments thereof, it should be understood that this invention is not limited to these embodiments and the the appended claims are intended to include these and other features and embodiments as may be devised by those skilled in the art which are nevertheless within the spirit and scope of this invention.

I claim:

1. Bag for storing blood components, consisting of a sterilizable, flexible closed container with means for hanging said container including an inlet-outlet fitment at the top thereof forming part of said closed container, said filament including a. an outlet consisting of a first hollow outward protrusion with a releasably secured cap, said first hollow outward protrusion including a plurality of circumferential ridges on its outer surface for sealingly engaging said cap, said cap being provided with mating annular grooves for engaging said plurality of circumferential ridges and stop means for limiting penetration of said first hollow outward protrusion therein, said ridges providing an interference fit with the interior of said cap, and b. at least one inlet consisting of a second hollow outward protrusion having on its outer diameter a circumferential raised portion.

* * * * *